United States Patent [19]

Hirano et al.

[11] Patent Number: 6,060,302
[45] Date of Patent: May 9, 2000

[54] HUMAN PHOSPHOLIPASE C-α AND DNA SEQUENCE ENCODING THE SAME

[75] Inventors: Naoto Hirano, c/o The Third Department of Internal Medicine, Faculty of Medicine, University of Tokyo, 3-1, Hongo 7-chome, Bunkyo-ku; Hisamaru Hirai, Tokyo, both of Japan

[73] Assignees: Shionogi & Co., Ltd., Osaka; Naoto Hirano, Tokyo, both of Japan

[21] Appl. No.: 08/627,907

[22] PCT Filed: Sep. 22, 1994

[86] PCT No.: PCT/JP94/01572

§ 371 Date: Mar. 22, 1996

§ 102(e) Date: Mar. 22, 1996

[87] PCT Pub. No.: WO95/08624

PCT Pub. Date: Mar. 30, 1995

[30] Foreign Application Priority Data

Sep. 24, 1993 [JP] Japan .................................. 5-238402

[51] Int. Cl.⁷ .................... C07K 14/00; C12N 15/63; C12N 1/20; C12N 15/00

[52] U.S. Cl. .................. 435/252.3; 530/350; 536/23.1; 536/23.2; 536/23.5; 435/69.1; 435/196; 435/198; 435/199; 435/252.33; 435/320.1

[58] Field of Search ..................... 435/199, 198, 435/196; 536/23.1, 23.2, 23.5; 435/6, 69.1, 252.3, 252.33, 320.1; 424/94.6; 514/17; 530/350

[56] References Cited

PUBLICATIONS

C. F. Bennett et al., "Molecular Cloning and Complete Amino–Acid Sequence of Form–I Phosphoinositide–specific Phospholipase C," *Nature*, 334, pp. 268–270 (1988).

R. B. Freedman, "Protein Disulfide Isomerase: Multiple Roles in the Modification of Nascent Secretory Proteins," *Cell*, 57, pp. 1069–1072 (1989).

W. M. Hempel et al., "Expression of Phospholipase C Isozymes By Murine B Lymphocytes," *J. Immunology*, 146, pp. 3713–3720 (1991).

H. Hirai et al., "SH2 Mutants of c–src That Are Host Dependent For Transformation Are trans–Dominant Inhibitors of Mouse Cell Transformation By Activated c–src," *Genes & Development*, 4, pp. 2342–2352 (1990).

H. Hirai et al., "Site–Directed Mutagenesis of the SH2– and SH3–Coding Domains of c–src Produces Varied Phenotypes, Including Oncogenic Activation of p60$^{c-src}$," *Molecular & Cellular Biol.*, 10, pp. 1307–1318 (1990).

H. Hirai et al., "Mutations in src Homology Regions 2 and 3 of Activated Chicken c–src That Result in Preferential Transformation of Mouse or Chicken Cells," *Proc. Natl. Acad. Sci.*, 87, 8592–8596 (1990).

N. Hirano et al., "Cloning of Bovine PLC–α and Biological Significance Thereof," *Extended Abstracts: The 15th Annual Meeting of the Japanese Society of Molecular Biology*, 4L–23 (1993). (partial English translation provided).

A. Holmgren, "Thioredoxin Glutaredoxin Systems," *J. Biol. Chem.*, 264, pp. 13963–13966 (1989).

Y. Takagi et al., "Confirmation of Gene," *Experimentation Methods for Gene Manipulation*, p. 167 (1980). (partial English translation provided).

*Primary Examiner*—Robert A. Wax
*Assistant Examiner*—Tekchand Saidha
*Attorney, Agent, or Firm*—Fish & Neave; James F. Haley, Jr.

[57] ABSTRACT

Genes encoding a human PLC-α polypeptide are provided. An expression vector containing these genes and a transformant having the expression vector are provided. The human PLC-α polypeptide can be produced by cultivating the transformant. The human PLC-α polypeptide is useful as an anti-inflammatory agent. Furthermore, a measurement system for conducting clinical evaluation of canceration can be constructed by using the PLC-α polypeptide.

5 Claims, 8 Drawing Sheets

FIG. 1A

```
bovine  -24  MRLRRLLALFPGLALLLAARLAAASDVLELTDDNFESRITDTGSSGLIVV
human        MRLRRLLALFPGVALLLAARLAAASDVLELTDDNFESRISDTGSAGLMLV
mouse        MRFSCLALLPGVALLLASARLAAASDVLELTDENFESRVSDTGSAGLMLV
rat          MPSAALRCSRAWRLLLASALLASASDVLELTDENFESRVSDTGSAGLMLV
              *   .  * ..*.* ** * *.****.*..* bovine   27  EFFAPWCGHCKRLAPEYEAAATRLKGIVPLAKVDCTANTNTCNKYGVSGY
human        EFFAPWCGHCKRLAPEYEAAATRLKGIVPLAKVDCTANTNTCNKYGVSGY
mouse        EFFAPWCGHCKRLAPEYEAAATRLK-IVPLAKVDCTANTNTCNKYGVSGY
rat          EFFAPWCGHCKRLAPEYEAAATRLKGIVPLAKVDCTANTNTCNKYGVTGY
             ************************* ********************.**

bovine   77  PTLKIFRDGEESGAYDGPRTADGIVSHLKKQAGPASVPLKSEEFEKFIS
human        PTLKIFRDGEEAGAYDGPRTADGIVSHLKKQAGPASVPLRTEEFKKFIS
mouse        PTLKIFRAGEEAGAYDGPRTADGIVSHLKKQAGPASVPLRTEEEFKKFIS
rat          PTLKIFRDGEEAGAYDGPRTADGIVSHLKKQAGPASVPLRTEDEFKKFIS
             *******.***..****************************..**.****
```

FIG. 1B

```
bovine  127  DKDASVVGFFKDLFSEAHSEFLKAASNLRDNYRFAHTNVESLVNKYDDDG
human        DKDASIVGFFDDSFSEAHSEFLKAASNLRDNYRFAHTNVESLVNEYDDNG
mouse        DKDASVVGFFRDLFSDGHSEFLKAASNLRDNYRFAHTNIESLVKEYDDNG
rat          DKDASVVGFFRDLFSDGHSEFLKAASNLRDNYRFAHTNVESLVKEYDDNG
             **. .  ****************.* .*.* bovine  177  EGITLFRPSHLTNKFEDKTVAYTEQKMTSGKIKRFIQENIFGICPHMTED
human        EGIILFRPSHLTNKFEEYKTVAYTEQKMTSGKIKKFIQENIFGICPHMTED
mouse        EGITIFRPLHLANKFEDKTVAYTEKKMTSAKIKKFIQDSIFGLCPHMTED
rat          EGITIFRPLHLANKFEDKIVAYTEKKMTSGKSRSLFRKA-FGLCPHMTED
             * ...**..*.*  ... .  .****** bovine  227  NKDLLQGKDLLIAYYDVDYEKNAKGSNYWRNRVMMVAKKFLDAGQKLHFA
human        NKDLIQGKDLLIAYYDVDYEKDAKGSNYWRNRVMMVAKKFLDAGHKLNFA
mouse        NKDLIQGKDLLTAYYDVDYEKNAKGSNYWRNRVMMVAKKFLDAGHKLNFA
rat          NKDLIQGKDLLTAYYDVDYEKNTKGSNYWRNRVMMVAKTFLDAGHKLNFA
             ****.****** ********. . **************.****.**.**

bovine  276  VASRKTFSHELSDFGLESTTGEIPVVAVRTAKGEKFVMQEEFSRDGKALE
human        VASRKTFSHELSDFGLESTAGEIPVVAIRTAKGEKFVMQEEFSRDGKALE
mouse        VASRKTFSHELSDFSLESTTGEVPVVAIRTAKGEKFVMQEEFSRDGKALE
rat          VASRKTFSHELSDFGLESTTGEIPVVAIRTAKGEKFVMQEEFSRDGKALE
             ************** ****.**.****.*********************
```

FIG. IC

```
bovine  327  RFLEDYFDGNLKRYLKSEPIPESNDGPVKVVAENFDEIVNNENKDVLIE
human        RFLQGYFGGNLKRYLKSDPIPESNDGPVKVVAENFDEIVNNENKDVLIE
mouse        QFLQEYFDGNLKRYLKSEPIPESNEGPVKVVAENFDDIVNEEDKDVLIE
rat          RFLQEYFDGNLKRYLKSEPIPETNEGPVKVVAESFDDIVNAEDKDVLIE
             *:*  :** :*::*****::  :***** bovine  377  FYAPWCGHCKNLEPKYKELGEKLRKDPNIVIAKMDATANDVPSPYEVRGF
human        FYAPWCGHCKNLEPKYKELGEKLSKDPNIVIAKMDATANDVPSPYEVRGF
mouse        FYAPWCGHCKNLEPKYKELGEKLSKDPNIVIAKMDATANDVPSPYEVKGF
rat          FYAPWCGHCKNLEPKYKELGEKLSKDPNIVIAKMDATANDVPSPYEVKGF
             **********************:**********************:**

bovine  427  PTIYFSPANKKQNPKKYEGGRELSDFISYLKREATNPPVIQEEKPKKKKK
human        PTIYFSPANKKLNPKKYEGGRELSDFISYLQREATNPPVIQEEKPKKKKK
mouse        PTIYFSPANKKLTPKKYEGGRELNDFISYLQREATNPPIIQEEKPKKKKK
rat          PTIYFSPANKKLTPKKYEGGRELNDFISYLQREATNPPIIQEEKPKKKKK
             *********  ******.**:**:******* bovine  477  AQEDL
human        AQEDL
mouse        AQEDL
rat          AQEDL
             *****
```

FIG. 2A

```
PLC-α  MRLRRLALFPGVALLLAAARLAAAASDVLELITDONFESRISDTGSAGLMLV
PDI    M-LRRALLCLPWSALVRADAPEEEDHVLVLRKSNFAEALAAHKYPP---V
       * ***  *     *        *  ** *             .

PLC-α  EFFAPWCGHCKRLAPEYEAAATRLKGI---VPLAKVDCTANTNTCNKYGV
PDI    EFHAPWCGHCKALAPEYAKAAGKLKAEGSEIRLAKVDATEESDLAQQYGV
       ** ******* *******  *  **       *****    *   ***

PLC-α  SGYPTLKIFRDGEEAGA--YDGPRTADGIVSHLKKQAGPASVPLRTEEEF
PDI    RGYPTIKFFRNGDTASPKEYTAGREADDIVNWLKKRTGPAATTLPDGAAA
        **** * * *         *   ** ** * **   ** *

PLC-α  KKFISDKDASIVGFFDDSFSEAHSEFLKAASNLRDNYRFAHTNVESLVNE
PDI    ESLVESSEVAVIGFFKDVESDSAKQFLQAAEAI-DDIPFGITSNSDVFSK
         :  .  . :**** * .* :: ** ::  :: *  :  :* *:*.

PLC-α  YDDNGEGIILFRPSHLTNKFEYKTVAYTEQKMTSGKIKKFIQENIFGICP
PDI    YQLDKDGVVLFK-----KFDEGRNNF-EGEVTKENLLDFIKHNQLPLVI
       *   .:*::**       *:      *  .**. : .** :*   ::
```

```
PLC-α    HMTEDNKDLIQGKD-----LL-----IAYYDVDYEKDAKGSNYWRNRVMM
PDI      EFTEQTAPKIFGGEIKTHILLFLPKSVSDYDGKLSNFKTAAESFKGKILF
         **                ..          **          *       ....

PLC-α    VAKKFLDAGHKLNFAVASRKTFSHELSDFGLESTAGEIPVVAIRTAKGE-
PDI      I---FIDSDHTDN------QRILEFGLKK--EECPAVRLITLEEEM
          *   ...*      *         ***      .    **     ***

PLC-α    -KFVMQEEFSRDGKALERFLQGYFGGNLKRYLKSDPIPES-NDGPVKVVV
PDI      TKYKPESE-ELTAERITEFCHRFLEGKIKPHLMSQELPEDWDKQPVKLV
          *        *   * ** ** *  ** *  *     ..*   * ** *

PLC-α    AENFDEIVNNENKDVLIEFYA[FWCGHCK]NLEPKYKELGEKLSKDPNIVIA
PDI      GKNFEDVAFDEKKNVFEFYA[PWCGHCK]QLAPIWDKLGETYKDHENIVIA
          :***:  : ::::* :****  ***** :*  :  :**     .*****

PLC-α    KMDATANDVPSPYEVRGFPTIYFSPANKKLNPKKYEGGRELSDFISYLQR
PDI      KMDSTANEV-EAVKVHGFPTLGFFPASADRTVIDYNGERTLDGFKKFLES
         ***.***:  .:  * .****  * * . ::::  ::** * .* . :

PLC-α    ---------EATNPPVIQEEKPKKKKAQEDL
PDI      GGQDGAGDVDDLEDLEEAEEPDMEEDDDQKAVK--DEL
                    *     ::*        :       **
```

```
PLC-α (25-129)   -SDVLELTDDNFESRISDTGSAGLMLVEFFAPWCGHCKRLAPEYEAAATRLKGIV-
thioredoxin     MVKQIE-SKTAFQEAL-DAAGDKLVVVDFSATWCGPCKMIKPFFHSLSEKYSNVIF
                 **  *   *        *    ***  *** ** * *    *

PLC-α (25-129)   -PLAKVDCTANTNTCNKYGVSGYPTLKIFRDGEEAGAYDGPRTA--DGIVSHLK
thioredoxin     KEVDVDDCQDVASECE---VKCMPTFQFFKKGQKVGEFSGANKEKLEATINELV
                 **    *           *   *  * *  *      *     *
```

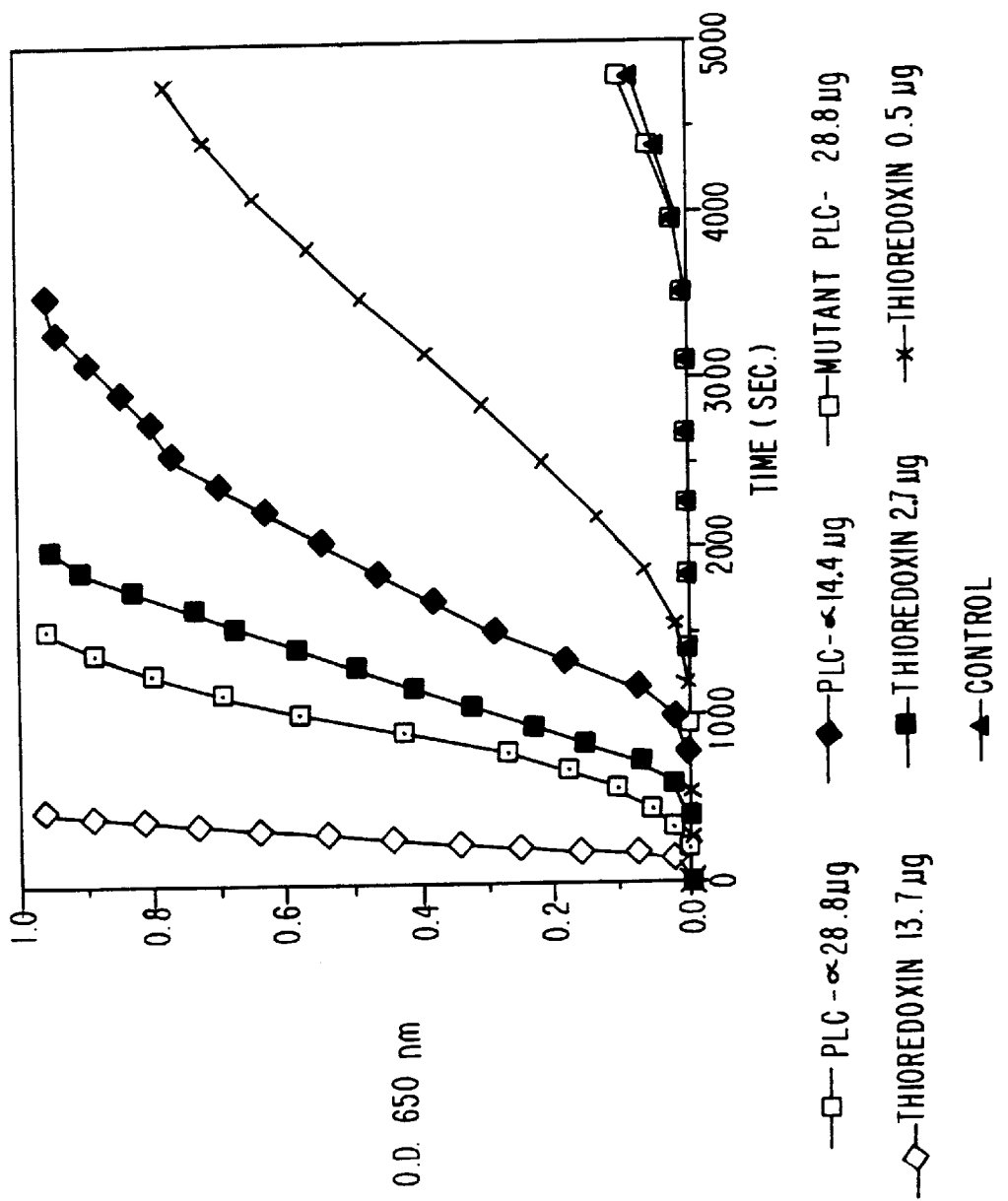

HUMAN PHOSPHOLIPASE C-α AND DNA SEQUENCE ENCODING THE SAME

This application is a 371 PCT/JP94/01572 filed Sep. 22, 1994.

TECHNICAL FIELD

The present invention relates to human phospholipase C-α, which is a secretory protein having an oxidation-reduction activity; genes encoding the human phospholipase C-α; an expression vector containing the genes; and a transformant having the expression vector.

BACKGROUND ART

Phospholipase C-α (hereinafter referred to as PLC-α) has conventionally been considered to belong to the superfamily of various isozymes of phospholipase C (hereinafter referred to as PLC).

PLC is an enzyme hydrolyzing (hereinafter referred to as a PLC activity) glycerophospholipid and sphingophospholipid; which is known to be present in the spleen, the tunica mucosa interstini tenuis, and the placenta, etc. of mammals and to play an important role in a living body. For example, phosphatidylinositol-specific phospholipase C (PI-PLC), which is widely present in a living body, hydrolyzes phosphatidylinositol 4,5-diphosphate to generate 1,2-diacylglycerol and inositol 1,4,5-triphosphate (Rhee, S.G. et al., Science 244, pp. 546–550 (1989)). There are a number of reports on various isozymes of PLC, for example, as follows: C. F. Bennett et al., Nature 334, pp. 268–270 (1988); Y. Emori et al., J. Biol. Chem. 264, pp. 21885–21890 (1989); M. Katan et al., Cell 54, pp. 171–177 (1988); S. Ohta et al., FEBS Lett. 242, pp. 31–35 (1988); M. L. Stahl et al., Nature 332, pp. 269–272 (1988); P. G. Suh et al., Cell 54, pp. 161–169 (1988); and R. W. Kritz et al., CIBA Found. Symp. 150, pp. 112–127 (1990).

In terms of function, the above-mentioned PLC-α is not well known; however, the expression thereof is known to increase in a living body being subject to stress and having cancerous tissue.

Regarding the PLC-α of mammals; those of mice (W. M. Hempel et al., J. Immunol. 146, pp. 3713–3720 (1991)), rats (C. F. Bennett et al., Nature 334, pp. 268–270 (1988)), and bovines (Hirano et al., Extended Abstracts, 4L-23, The 15th Annual Meeting of The Japanese Society of Molecular Biology, 1992), have been reported. The PLC-α of these mammals does not have significant homology with any of known sequences of the other known PLC family members.

The PLC-α of the above-mentioned mammals has a conserved amino acid sequence, Trp-Cys-Gly-His-Cys-Lys, [SEQ ID NO:5] at two places. This conserved amino acid sequence is identical with or very similar to the amino acid sequence of an active site for oxidation-reduction activity of protein disulfide isomerase (PDI) and thioredoxin. PDI and thioredoxin are both multifunctional proteins which function as protein disulfide reductase and isomerase, and catalyze the conversion of a thiol group to a disulfide group. PDI of mammals has two conserved sequences in its amino acid sequence, which are homologous to the above-mentioned PLC-α. Thioredoxin of prokaryotes and eukaryotes has one sequence, Trp-Cys-Gly-Pro-Cys-Lys, [SEQ ID NO:6]in its amino acid sequence which is similar to the conserved sequence as shown above. Cys residues in these sequences are respectively assumed to be active sites of catalytic activity (A. Holmgren, J. Biol. Chem. 264, pp. 13963–13966; R. B. Freedman, Cell 57, pp. 1069–1702).

The inventors of the present invention have found that bovine PLC-α expressed in E. coli is a secretory protein which does not functionally have PLC activity and has the activity of reducing a disulfide bond of protein such as insulin (Hirano et al., Cloning of bovine PLC-α and biological significance thereof, Extended Abstracts, 4L-23, The 15th Annual Meeting of The Japanese Society of Molecular Biology, 1992). Thus, PLC-α is not supposed to belong to the PLC superfamily but to the oxidation-reduction control protein family; and its nomenclature has accordingly been changed to thymuredoxin (Hirano et al. supra). This is supported by the above-mentioned consensus of the sequence.

The oxidation-reduction control protein family including PLC-α, thioredoxin, PDI, etc. is considered to be required for maintaining the normal function of a living body. Hereinafter, findings obtained from various reports on various members of the oxidation-reduction control protein family will be shown.

PLC-α has its expression level increased in animal cells transformed with oncogenes, v-src gene; therefore, it is considered to be related to carcinogenesis (H. Hirai et al., Genes Dev 4, pp. 2342–2352 (1990), Mol. Cell. Biol. 10, pp. 1307–1318 (1990), Proc. Natl. Acad. Sci. U.S.A. 87, pp. 8592–8596 (1990)).

Human thioredoxin, also called adult T-cell leukemia (ATL) derived factor, is known to induce the expression of interleukin-2 receptor and stimulate the multiplication of cells (Y. Tagaya et al., EMBO J. 8, pp. 757–764 (1989)).

The protein level of thioredoxin is generally high in actively expanding tissue and the mRNA level of thioredoxin increases (S. W. Jones et al., J. Biol. Chem. 263, pp. 9607–9611 (1988)). As one of functional mechanisms maintaining the normal cell morphology and function of the oxidation-reduction protein control family, controls of the relationships between DNA and protein and between proteins through a Cys residue are considered. This is described in the following document incorporated in the present specification for reference.

The binding of fos and Jun heterodimers to DNA, which relates to v-jun genes and v-fos genes having activity as oncogenes, is regulated by the oxidation-reduction control of a conserved Cys residue in a DNA binding region of these two kinds of proteins: thioredoxin can catalyzes this regulation (C. Abate et al., Science 249, pp. 1157–1161 (1991)). Receptor type tyirosinekinase (1tk) is regulated through the change in a cell oxidation-reduction ability, and kinase activity thereof is increased by the formation of a multimer composed of disulfide bonds (A. R. Bauskin et al., Cell 66, pp. 685–696 (1991)).

Although a control factor of a Cys mediated oxidation-reduction ability in vivo has not been identified, PLC-α, thioredoxin, and PDI have a thiol-dependent catalytic activity because of a sequence Trp-Cys-Gly-His-Cys-Lys[SEQ ID NO:] or Trp Cys-gly-Pro-Cys-Lys [SEQ ID NO:6] therefore, there is a possibility that these are control factors.

DISCLOSURE OF THE INVENTION

As described above, PLC-α of mice, rats, and bovines was reported in detail, whereas no reports were found relating to human beings. Therefore, a human PLC-α protein and a DNA sequence encoding the same have been demanded. The present invention solves the above-mentioned conventional problems and its objective is to provide human PLC-α, human PLC—genes, an expression vector containing the genes, and a transformant having the expression vector.

The inventors of the present invention obtained bovine csk protein (S. Noda et al., *Nature* 351, pp. 69–72 (1991)) from a bovine thymus, partially purified it, and prepared a rabbit polyclonal antiserum against the purified protein. A bovine thymus cDNA library was screened with the antiserum to find a DNA sequence encoding bovine PLC-α genes. Furthermore, we isolated human PLC-α cDNA from a human placenta cDNA library by hybridization using bovine PLC-α cDNA, thereby achieving the present invention.

The polypeptide of the present invention contains an amino acid sequence from Ser at the 25st position to Leu in the 505th position of SEQ ID NO: 2 of the Sequence Listing.

The DNA sequence of the present invention encodes an amino acid sequence from Ser at the 25st position to Leu in the 505th position of SEQ ID NO: 2 of the Sequence Listing.

The expression vector of the present invention has the above-mentioned DNA sequence.

The transformant of the present invention is obtained by introducing the above-mentioned expression vector into a host.

BRIEF DESCRIPTION OF THE DRAWINGS

FIG. 1 shows amino acid sequences of PLC-α genes of a bovine, a human being, and a mouse.

FIG. 2 shows amino acid sequences of human PLC-α genes and human PDI genes.

FIG. 3 shows amino acid sequences of human PLC-α genes and human thioredoxin genes.

FIG. 5 shows measurements of activities to decompose insulin, of wild-type and mutant bovine PLC-α proteins produced in *E. coli* transformed with wild-type and mutant bovine PLC-α genes.

BEST MODE FOR CARRYING OUT THE INVENTION

Figure 4A:
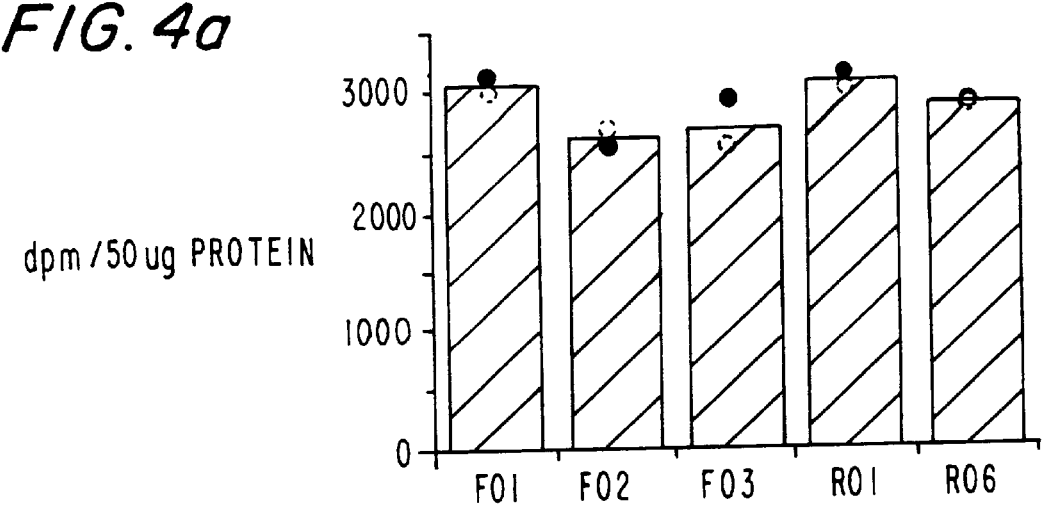
FIG. 4 shows measurements of PLC activities in a crude extract, a cytoplasmic fraction, and a membrane fraction of animal cells transformed with bovine PLC-α genes.

The polypeptide and the DNA sequence encoding the same according to the present invention can be prepared, for example, in accordance with the following steps.
(1) Preparation of Human Placenta cDNA Library A human placenta cDNA library can be prepared by a conventional method. First, total RNA is isolated from a human placenta by, for example, a guani-dine-phenol/chloroform method (*Gene*, 28 (1984), pp. 263–270), and the isolate is repeatedly subjected to oligo dT cellulose column chromatography to obtain polyA RNA. Double-stranded cDNA is synthesized from the RNA thus obtained. The synthesis of the double-stranded cDNA can be conducted by, for example, a method of Gubler and Hoffman (*Gene*, 25 (1983), pp. 263–269). An appropriate linker sequence is attached to the double-stranded cDNA thus obtained to form a restriction enzyme cleavage site. Then, the resultant cDNA is inserted into a restriction enzyme Cleavage site of a cloning vector, which is the same as that of the linker sequence, whereby a human placenta cDNA library is prepared. As a cloning vector, a phage vector such as λgt11 is preferably used; however, the cloning vector is not limited thereto and any of the cloning vectors known to those skilled in the art can be used.
(2) Preparation of bovine PLC-α cDNA (i) Partial Purification of Bovine csk Protein Bovine csk protein can be partially purified from a bovine thymus by a purification method known to those skilled in the art, e.g., the method of Noda et al.

(ii) Preparation of Polyclonal Antiserum

Polyclonal antiserum can be prepared by a method known to those skilled in the art by, for example, immunizing a rabbit with partially purified bovine csk protein, collecting serum from the rabbit, and partially purifying the serum by ammonium sulfate fractionation. Synthesized bovine csk protein or a fragment thereof can be used in place of the partially purified bovine csk protein.

(iii) Preparation of Bovine Thymus cDNA Library

A bovine thymus cDNA library can be prepared, using a bovine thymus as a material by a conventional method, as in the above-mentioned (1) Preparation of human placenta cDNA library.

(iv) Isolation of Bovine Thymus cDNA Phage Clones

The analysis of the bovine thymus cDNA library obtained in the above (iii) can be conducted by screening plaques derived from phage in which the bovine thymus cDNA has been inserted, with the polyclonal antiserum obtained in the above (ii), using, for example, ProtoBlot system (produced by Promega). Thus, positive phage clones containing the bovine PLC-α protein DNA fragment can be isolated.

(v) Sequencing of Bovine Thymus cDNA

Sequencing of the DNA insert of the positive phage clones obtained in the above (iv) can be conducted directly by a method known to those skilled in the art, for example, using a DNA sequencing kit. Alternatively, sequencing can be conducted by using phage DNA containing the DNA insert prepared from the clones. The preparation of the phage DNA containing the DNA insert can be conducted by, for example, a protocol of Maniatis et al., Molecular Cloning, A Laboratory manual, Cold Spring Harbor Laboratory Press, New York (1982). The DNA sequence of the bovine thymus cDNA clones thus sequenced and the amino acid sequence corresponding thereto are shown in SEQ ID NO: 3 of the Sequence Listing.
(3) Isolation of Human Thymus cDNA Phage Clones Positive phage clones containing a human PLC-α DNA fragment can be isolated by screening the human placenta cDNA library obtained in the above (1) using bovine PLC-α cDNA labelled with $^{32}P$ as a probe under moderate hybridization conditions. The bovine PLC-α cDNA probe labelled with $^{32}p$ can be prepared based on the sequence determined in the above (v) by a method known to those skilled in the art.
(4) Sequencing of Human Thymus cDNA Phage Clones Sequencing of the DNA insert of the positive phage clones obtained in the above (3) can be conducted by the same method as that of the above (v). The DNA sequence of the human thymus cDNA clones thus determined and the amino, acid sequence corresponding thereto are shown in SEQ ID NO: 1 of the Sequence Listing.
(5) Production of Human PLC-α Protein Human PLC-α protein can be produced by a genetic recombination technique using a host/expression vector known to those skilled in the art. A number of kinds of combinations between a host and an expression vector can be used for expressing the human PLC-α protein of the present invention. For example, effective expression vectors can contain segments of chromosomes, non-chromosomes, and a synthetic DNA sequence. Various known derivatives of SV40 and known bacterial plasmids are preferable as the vector. Specific examples of the vector include *E. coli* plasmids such as pCR1, pBR322, pMB9, pET-3A, and derivatives thereof; broad-range host plasmid RP4; a number of derivatives of λ-phage; phage DNA such as M13 and filamentous single-stranded phage DNA; yeast plasmids such as 2 μplasmid or derivatives thereof; and plasmids containing an adenovirus major late promoter enhanced in the presence of SV40 enhancer.

Furthermore, a number of kinds of expression regulatory sequences, i.e., sequences regulating the expression of a DNA sequence when being operably bound by the DNA sequence, can be used in the above-mentioned vector for expressing the human PLC-α protein of the present invention. Examples of such useful expression regulatory sequences include early and late promoters of SV40; early promoters of adenovirus or cytomegalovirus; the lac system; the trp system; the TAC or TRC system; the T7 promoter which is expressed by T7 RNA polymerase; a major operator region and a promoter region of λ-phage; a regulatory region of fd-coated protein; promoters of 3-phosphoglyceratekinase or other glycolytic pathway enzymes; acid phosphatase such as Pho5 promoter, a promoter of yeast α-factor, and polyhedron promoter of Baculovirus; other known sequences regulating the expression of genes of prokaryotic cells, eukaryotic cells, or viruses thereof; and various combinations thereof.

A number of kinds of single-cell host cells are useful for the expression of the human PLC-α protein of the present invention. Examples of the hosts can include *E. coli*; Pseudomonas; Bacillus; Streptomyces; Saccharomyces and other strains of fungi; Chinese hamster ovary ("CHO") cells and cultivated mouse cells; animal cells such as COS1, COS7, BSC1, BSC40, and BMT10 of the African green monkey; known eukaryotic cells such as cultivated insect cells, cultivated human cells, cultivated plant cells; and procaryotic cells.

A vector having a DNA sequence of the above human PLC-α polypeptide is introduced into a host to obtain a transformant. A human PLC-α polypeptide can be produced by cultivating the transformant in an appropriate culture medium.

According to the present invention, as described above, human PLC-α which is a secretory protein having oxidation-reduction activity, human PLC-α genes, an expression vector containing the genes, and a transformant halving the expression vector are provided.

The polypeptide of the present invention has a conserved sequence which is identical with or very similar to an active site of thioredoxin stimulating the multiplication of cells and has an activity of reducing a disulfide bond of protein, and can therefore be utilized as an anti-inflammatory agent. Furthermore, the expression of PLC-α increases in a living body which is cancerated or is subject to stress, so that PLC-α functions as an indicator of these conditions and can provide a measurement system of clinical evaluation of these conditions.

EXAMPLES

Hereinafter, the present invention will be described by way of illustrative examples.

Example 1

(1) Preparation of Human Placenta cDNA Library

The first strand and the second strand of cDNA were synthesized from polyA RNA prepared from a human placenta. EcoRI-NotI-BamHI adaptors were attached to both ends of the double-stranded DNA thus obtained. The resultant DNA was inserted into vector λZAPII to prepare a human placenta cDNA library.

(2) Preparation of Bovine PLC-α cDNA (i) Partial Purification of Bovine csk Protein A peptide having an amino acid sequence Gly-Thr-Phe-Leu-Val-Arg-Glu-Ser which is a part of csk protein and is conserved in an SH2 (Src.Homology2) portion common to the src protein family was synthesized. Antiserum against this peptide was prepared from a rabbit. Then csk, which is 50 kD protein partially purified from a bovine thymus, was obtained by Western blotting method using this antiserum.

(ii) Preparation of Polyclonal Antiserum

A rabbit was immunized with partially purified bovine csk protein, and serum was collected from the rabbit. The serum was partially purified by ammonium sulfate fractionation to obtain antiserum. The antiserum thus obtained was named polyclonal antiserum 507.

(iii) Preparation of Bovine Thymus cDNA Library

The first strand and the second strand of cDNA were synthesized from polyA RNA prepared from a bovine thymus. EcoRI linkers were attached to both ends of the double-stranded DNA thus obtained. The resultant DNA was inserted into an EcoRI site of vector λgt11 to obtain a cDNA library.

(iv) Isolation and Sequencing of Bovine Thymus cDNA clones

The analysis of the bovine thymus cDNA library obtained in the above (iii) was conducted by screening $1.8 \times 10^6$ plaques derived from phage λgt11 in which the bovine thymus cDNA was inserted, with polyclonal antiserum507 using the ProtoBlot system (produced by Promega), whereby 3 positive phage clones were isolated. More specifically, the above cDNA library was plated with *E. coli* Y1090R⁻ and was cultivated at 43° C. for 4 hours until small plaques were generated. Thereafter, a nitrocellulose sheet (Hybond C-Extra, produced by Amersham) previously soaked in IPTG inducing the expression from lac promoter of vector λ11gt was placed on the plate containing these small plaques. The plate was kept warm for 3 hours. Then, the nitrocellulose sheet was carefully peeled off and positive phage clones reactive to polyclonal antiserum 507 were identified.

Both strands of phage clone λ12 having the largest insert of 1.8 kb of the phage clones obtained in the above (iv) were sequenced with Sequenase 2.0 (produced by USB) by generating nested deletions at each strand with Exonuclease III (produced by Pharmacia).

The homology between the determined sequence and the known sequence was examined by using a DDBJ (DNA Data Bank of Japan) database in accordance with FASTA and TFASTA programs (W. R. Peason et al., *Proc. Natn. Acad. Sci. U.S.A.* 85, pp. 2444–2448 (1988)). As a result, the determined sequence was found to be a DNA sequence similar to that of bovine PLC-α but lacking a 5'-portion. The same library was screened using an EcoRI-EcoRV fragment (positioned closest to the 5'-terminus of a phage clone λ12 insert) of the phage clone λ12 insert, whereby phage clone λ21 having a DNA insert longer than, a phage clone λ12 insert was obtained. The sequence of the insert of the phage clone λ211 thus obtained was determined in the same manner as the above and indicated that the phage clone λ21 contained full length sequence of a bovine PLC-α having the 5'-portion sequence. The full length DNA sequence of bovine PLC-α thus obtained and the amino acid sequence corresponding thereto are shown in SEQ ID NO: 3 of the Sequence Listing.

(3) Isolation of Human Placenta cDNA Phage Clones

In order to obtain a human PLC-α cDNA phage alone, the λZAPII human placenta cDNA library obtained in the above (1) was screened using the DNA insert of the phage clone λ21 labelled with $^{32}$p as a probe under the moderate hybridization conditions to obtain positive phage clones named λ17. The sequence of the insert in the phage clone thus obtained was determined by the same method as that of the above (1)(v). The full length DNA, sequence of human PLC-α thus obtained and the amino acid sequence corresponding thereto are shown in SEQ ID NO: 1 of the Sequence Listing.

The determined amino acid sequences of bovine and human PLC-α and the amino acid sequence of the known mouse PLC-α (Hempel et al, supra) are shown in FIG. 1. The bovine and human PLC-α cDNA sequences thus obtained were composed of 1515 bp of open reading frame and encoded a polypeptide including 505 amino acids having a hydrophobic N-terminal signal peptide (amino acid residues 24 to 1). The molecular weight of the respective polypeptides were calculated to be 56,895 Da and 56,698 Da. The amino acid sequence of bovine PLC-α had 90%, 87%, and 94% homology with mouse, rat, and human PLC-α sequences, respectively.

FIG. 2 shows the determined human PLC-α and the known human protein disulfide reductase (hereinafter, referred to as PDI) (T. Pihlajaniemi et al., *EMBO J.* 6, pp. 643–649 (1987)). The human PLC-α had 56% homology and 32% similarity with human PDI at an amino acid level.

FIG. 3 shows the determined human PLC-α sequence and the known human thioredoxin sequence. The amino acids from the 1st to 105th positions of the human PLC-α sequence showed 55% homology and 23% similarity with human thioredoxin (Y. Tagaya et al., *EMBO J.* 8, pp. 757–764 (1989)).

Example 2

Sense vector PLC-α (expression vector) in which the bovine PLC-α cDNA sequence obtained in Example 1 was inserted downstream of a β-actin promoter of the mammal cell expression vector pUC-CAGGS in the forward direction and an antisense vector in which the bovine PLC-α cDNA sequence was inserted in the reverse direction were constructed. NIH3T3 mouse fibroblast was transformed together with pSV2NEO, using the sense vector and the antisense vector by a calcium phosphate coprecipitation method known to those skilled in the art. The transformant thus obtained was selected with 800 μg/ml of G418, whereby three kinds of independent stable transformants (named F01, F02, and F03) in which a sense vector is introduced and which expresses bovine PLC-α protein at a high level and two kinds of independent transformants (named R01 and R06) in which the antisense vector is introduced were obtained.

The cells of the transformants F01, F02, F03, R01, and R06 thus obtained were collected and dissolved in an ice-cooled cell lysing solution containing 50 mM of Tris-HCl (pH 7.4), 150 mM of NaCl, 0.05% (W/V) sodium dodecyl sulfate, 1% (v/v) triton X-100, 10 U/ml of aprotinin, 2 mM of PMSF, 100 mg/l of leupeptin, and 1 mM of ortho-vanadyl sodium. The solution thus obtained was subjected to SDS-PAGE using 9% acrylamide and transferred to a polyvinylidene difluoride film (produced by Millipore). The PLC-α expression level of three kinds of cell lines was measured by immunoblotting using polyclonal antiserum 507. The PLC-α expression level of three kinds of stable transformants is 10 to 15 times as high as endogenous PLC-α.

Figure 4B:
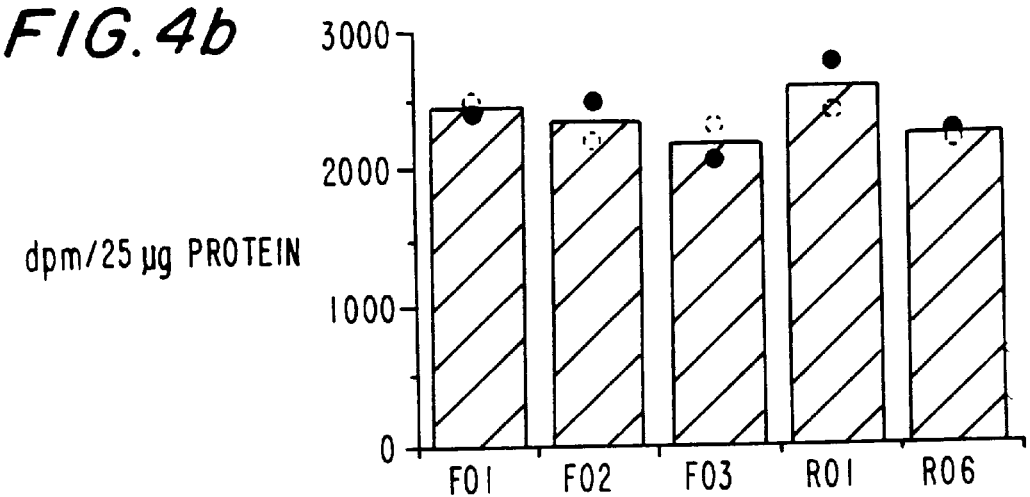
Figure 4C:
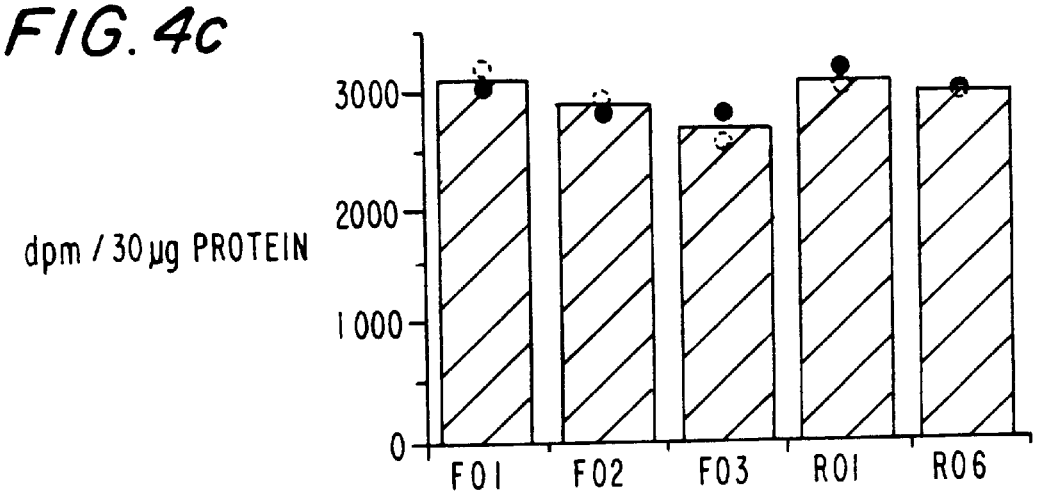

A crude extract, a cytoplasmic fraction, and a membrane fraction of these five cell lines were prepared in accordance with a method of Kato et al. (*J. Biol. Chem.* 267, pp. 6483–6487 (1991)). The PLC activity in the crude extract, the cytoplasmic fraction, and the membrane fraction thus obtained was measured by the method of Kato et al. using [$^3$H]PtdIns 4,5-$P_2$ as a substrate. FIG. 4 shows the measurement result. In this figure, a presents the PLC activity of the crude extract, b presents that of in the cytoplasmic fraction, and c presents that of the membrane fraction. As shown in this figure, in any of the fractions, the PLC activities were not substantially different among the respective cell lines.

Example 3

Mammal PLC-α has an amino acid sequence which is completely the same sequence as that of an oxidation-reduction active site of PDI in its amino acid sequence; therefore, the PLC-α was assumed to have the reduction function similar to that of PDI. The reduction function of wild-type and mutant bovine PLC-α proteins expressed in *E. coli* was measured by a known assay (A. Holmgren, *J. Biol. Chem.* 254, pp. 9627–9632 (1979)) for measuring the decomposition of insulin in dithiothreitol.

(1) Expression of Bovine PLC-α Protein

First, 1.8 kb of insert of phage clone λ12 obtained in Example 1 was treated with Mung bean nuclease so as to obtain blunt ends. The fragment thus obtained was subcloned at a SmaI site of bacterial expression vector pGEX2T (produced by Pharmacia) to construct plasmid pGEX-PLC-α. *E. coli* XL-1B was transformed with this plasmid. The transformant thus obtained was cultivated overnight by a conventional method, and the culture broth thus obtained was diluted with a fresh medium at a dilution rate of 1:10, followed by being cultivated at 25° C. Eighteen hours later, 0.1 ml of IPTG was added to the culture broth and the resultant culture solution was cultivated for another 6 hours; whereby, the expression of 1.8 kb insert was induced. The *E. coli* cells were lysed in a lysing buffer containing 50 mM of Tris-HCl (pH 7.5), 25% sucrose, 0.5 NP-40, and 5 mM of MgC'$_2$ by freeze-thawing. The lysate was purified by centrifugation to obtain supernatant. The supernatant was filtrated with 1.2 μm Acrodisc (produced by GelmanSciences), and the filtrate thus obtained was subjected to glutathione Sepharose 4B (produced by Pharmacia) column. The column was washed with a buffer containing 20 mM of Tris-HCl (pH 7.5), 2 mM of MgCl$_2$, and 1 mM of dithiothreitol. The filtrate was eluted with an elution buffer containing 5 mM glutathione and 50 mM of Tris-HCl (pH 9.5). The eluate was fractionated by 1.5 ml portions, followed by being analyzed by electrophoresis using an 8% SDS-polyacrylamide gel. Fractions containing PLC-α protein were collected and dialyzed against a dialysis buffer containing 20 mM of Tris-HCl (pH 7.5) and 10 mM of dithiothreitol. The dialyzed sample was incubated with a digestive buffer containing 2.5 mM of CaCl$_2$ 50 mM of Tris-HCl (pH 7.5), 150 mM of NaCl, and 400 U of human thrombin per milligram of protein at room temperature for 1.5 hours. This sample liquid was subjected to Sephadex 16/60 (produced by Pharmacia) equilibrated with a phosphate buffer and was eluted at 1 ml/min. The fractions thus obtained were analyzed with 12% SDS-PAGE and fractions containing bovine PLC-α protein were collected. The fractions thus collected were dialyzed against water and lyophilized to obtain PLC-α protein. This protein is wild-type PLC-α.

Then, a conserved sequence, Trp-Cys-Gly-His-Cys-Lys, was subjected to specific site-directed mutation in order to prepare a mutant PLC-α DNA sequence. The site-directed mutagenesis was conducted by using the Muta-Gene Kit (produced by Bio-Rad). Mutagenic primers, 5'GCCCCCTGGT CTCCACACAG CAAAAAGCTT [SEQ ID NO:7] (sense) and GCTCCTTGGT CTGGTCACTC TAAGAATCTG [SEQ ID NO:8] (sense), change Cys at the 57th and 60th positions into Ser, and Cys at the 406th and 409th positions into Ser, respectively. The site-directed mutagenesis thus obtained was confirmed by determining the base sequence. In the mutant PLC-α protein, in both of the two conserved sequences 4 Cys residues in total were replaced by Ser. More specifically, the mutant PLC-α protein has two Trp-Ser-Gly-His-Ser-Lys [SEQ ID NO:5] sequences. The mutant PLC-α DNA sequence was expressed in E. coli in the same way as in the wild-type PLC-α DNA sequence to obtain a mutant PLC-α protein.

(2) Standard Assay for Measuring Decomposition of Insulin

Assay for measuring the decomposition of insulin was conducted in the same way as in Holgeman et al. (supra) except that the reaction volume was 60 μl. Nonenzymatic decomposition of insulin with dithiothreitol was recorded as a control. E. coli thioredoxin was purchased from Promega.

The measurement result of the standard assay is shown in FIG. 5. In this figure, as represented by curves of closed circles and open squares with a dot, wild-type bovine PLC-α had an activity for reducing insulin; as represented by a curve of open squares, mutant bovine PLC-α did not have an activity for reducing insulin. In this assay, thioredoxin represented by curves of open squares and closed squares had an activity 2 to 3 times that of bovine PLC-α per mole of protein.

As is apparent from these results, it was found that PLC-α has an ability of catalyzing the reduction of disulfide bonds in the same way as in thioredoxin, and two Cys residues in the sequence Trp-Cys-Gly-His-Cys-Lys [SEQ ID NO:5] are indispensable for oxidation-reduction activity.

Example 4

Secretory PLC-α produced by the transformants F02 and R06 obtained in Example 2 was detected. F02 and R06 transformant cells were grown in 150 mm culture plates each containing DMEM culture medium (produced by GIBCO) with 10% bovine serum added. The grown cells were washed with a phosphate buffer and cultivated in 20 ml serum-free culture medium (Cell Grosser P. Sumitomo Pharmaceuticals Co.). Ten hours later, culture medium was collected and centrifuged at 4° C., 100,000 g for 1 hour, and then supernatant was recovered. The supernatant was dialyzed against water, followed by being lyophilized. Thereafter, immunoblotting was conducted using polyclonal antiserum 507 in the same way as in Example 2, whereby secretory PLC-α was detected. Immunoblotting indicated that an excess amount of secretory PLC-α was produced in the supernatant of the F02 cell, and a small amount of secretory PLC-α was even produced in the R06 cell.

Furthermore, the F02 and R06 transformant cells grown in the culture plates by the same method as the above were washed in DMEM culture medium containing no methionine. Those cells were labelled in vivo with [$^{35}$S]Met of 1 mCi at 37° C. in DMEM culture medium which contained 15 ml of 1% dialyzed bovine serum and did not contain methionine. The culture supernatant of the transformant cell labelled in vivo was obtained by cultivating with the same method as that of Example 4. The culture supernatant thus obtained was subjected to 9% SDS-PAGE and exposed to Fuji Bass Imaging Plate c (produced by Fuji) to detect secretory PLC-α. As a result, it was confirmed that PLC-α was secreted at a high level in the culture supernatant.

---

We claim:

1. An isolated human phospholipase C-α polypeptide comprising an amino acid sequence from Ser at position 25 to Leu at the position 505 of SEQ ID NO: 2.

2. A polypeptide according to claim 1, comprising an amino acid sequence from Met at the position 1 to Leu at position 505 of SEQ ID NO: 2.

3. A DNA sequence encoding the polypeptide of claim 1 or 2.

4. An expression vector comprising the DNA sequence of claim 3.

5. A transformed host cell obtained by introducing the expression vector of claim 4.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 1933 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 68..1585

(xi) SEQUENCE DESCRIPTION: SEQ ID NO:1:

```
GGCGCCGACC  TCCGCAGTCC  CAGCCGAGCC  GCGACCCTTC  CGGCCGTCCC  CACCCCACCT        60

CGCCGCC ATG CGC CTC CGC CGC CTA GCG CTG TTC CCG GGT GTG GCG CTG             109
        Met Arg Leu Arg Arg Leu Ala Leu Phe Pro Gly Val Ala Leu
         1               5                   10

CTT CTT GCC GCG GCC CGC CTC GCC GCT GCC TCC GAC GTG CTA GAA CTC             157
Leu Leu Ala Ala Ala Arg Leu Ala Ala Ala Ser Asp Val Leu Glu Leu
 15                  20                  25                  30

ACG GAC GAC AAC TTC GAG AGT CGC ATC TCC GAC ACG GGC TCT GCG GGC             205
Thr Asp Asp Asn Phe Glu Ser Arg Ile Ser Asp Thr Gly Ser Ala Gly
                 35                  40                  45

CTC ATG CTC GTC GAG TTC TTC GCT CCC TGG TGT GGA CAC TGC AAG AGA             253
Leu Met Leu Val Glu Phe Phe Ala Pro Trp Cys Gly His Cys Lys Arg
         50                  55                  60
```

-continued

| | |
|---|---|
| CTT GCA CCT GAG TAT GAA GCT GCA GCT ACC AGA TTA AAA GGA ATA GTC<br>Leu Ala Pro Glu Tyr Glu Ala Ala Ala Thr Arg Leu Lys Gly Ile Val<br>65                         70                     75 | 301 |
| CCA TTA GCA AAG GTT GAT TGC ACT GCC AAC ACT AAC ACC TGT AAT AAA<br>Pro Leu Ala Lys Val Asp Cys Thr Ala Asn Thr Asn Thr Cys Asn Lys<br>     80                    85                    90 | 349 |
| TAT GGA GTC AGT GGA TAT CCA ACC CTG AAG ATA TTT AGA GAT GGT GAA<br>Tyr Gly Val Ser Gly Tyr Pro Thr Leu Lys Ile Phe Arg Asp Gly Glu<br>95                       100                 105               110 | 397 |
| GAA GCA GGT GCT TAT GAT GGA CCT AGG ACT GCT GAT GGA ATT GTC AGC<br>Glu Ala Gly Ala Tyr Asp Gly Pro Arg Thr Ala Asp Gly Ile Val Ser<br>              115                120               125 | 445 |
| CAC TTG AAG AAG CAG GCA GGA CCA GCT TCA GTG CCT CTC AGG ACT GAG<br>His Leu Lys Lys Gln Ala Gly Pro Ala Ser Val Pro Leu Arg Thr Glu<br>     130                   135               140 | 493 |
| GAA GAA TTT AAG AAA TTC ATT AGT GAT AAA GAT GCC TCT ATA GTA GGT<br>Glu Glu Phe Lys Lys Phe Ile Ser Asp Lys Asp Ala Ser Ile Val Gly<br>         145                150               155 | 541 |
| TTT TTC GAT GAT TCA TTC AGT GAG GCT CAC TCC GAG TTC CTA AAA GCA<br>Phe Phe Asp Asp Ser Phe Ser Glu Ala His Ser Glu Phe Leu Lys Ala<br>     160                   165               170 | 589 |
| GCC AGC AAC TTG AGG GAT AAC TAC CGA TTT GCA CAT ACG AAT GTT GAG<br>Ala Ser Asn Leu Arg Asp Asn Tyr Arg Phe Ala His Thr Asn Val Glu<br>175                       180                 185               190 | 637 |
| TCT CTG GTG AAC GAG TAT GAT GAT AAT GGA GAG GGT ATC ATC TTA TTT<br>Ser Leu Val Asn Glu Tyr Asp Asp Asn Gly Glu Gly Ile Ile Leu Phe<br>              195                200               205 | 685 |
| CGT CCT TCA CAT CTC ACT AAC AAG TTT GAG TAC AAG ACT GTG GCA TAT<br>Arg Pro Ser His Leu Thr Asn Lys Phe Glu Tyr Lys Thr Val Ala Tyr<br>         210                215               220 | 733 |
| ACA GAG CAA AAA ATG ACC AGT GGC AAA ATT AAA AAG TTT ATC CAG GAA<br>Thr Glu Gln Lys Met Thr Ser Gly Lys Ile Lys Lys Phe Ile Gln Glu<br>         225                230               235 | 781 |
| AAC ATT TTT GGT ATC TGC CCT CAC ATG ACA GAG GAC AAT AAA GAT TTG<br>Asn Ile Phe Gly Ile Cys Pro His Met Thr Glu Asp Asn Lys Asp Leu<br>     240                   245               250 | 829 |
| ATA CAG GGC AAG GAC TTA CTT ATT GCT TAC TAT GAT GTG GAC TAT GAA<br>Ile Gln Gly Lys Asp Leu Leu Ile Ala Tyr Tyr Asp Val Asp Tyr Glu<br>255                       260               265               270 | 877 |
| AAG GAC GCT AAA GGT TCC AAC TAC TGG AGA AAC AGG GTA ATG ATG GTG<br>Lys Asp Ala Lys Gly Ser Asn Tyr Trp Arg Asn Arg Val Met Met Val<br>              275                280               285 | 925 |
| GCA AAG AAA TTC CTG GAT GCT GGG CAC AAA CTC AAC TTT GCT GTA GCT<br>Ala Lys Lys Phe Leu Asp Ala Gly His Lys Leu Asn Phe Ala Val Ala<br>         290                295               300 | 973 |
| AGC CGC AAA ACC TTT AGC CAT GAA CTT TCT GAT TTT GGC TTG GAG AGC<br>Ser Arg Lys Thr Phe Ser His Glu Leu Ser Asp Phe Gly Leu Glu Ser<br>     305                   310               315 | 1021 |
| ACT GCT GGA GAG ATT CCT GTT GTT GCT ATC AGG ACT GCT AAA GGA GAG<br>Thr Ala Gly Glu Ile Pro Val Val Ala Ile Arg Thr Ala Lys Gly Glu<br>320                       325                 330 | 1069 |
| AAG TTT GTC ATG CAG GAG GAG TTC TCG CGT GAT GGG AAG GCT CTG GAG<br>Lys Phe Val Met Gln Glu Glu Phe Ser Arg Asp Gly Lys Ala Leu Glu<br>335                       340               345               350 | 1117 |
| AGG TTC CTG CAG GGT TAC TTT GGT GGC AAT CTG AAG AGA TAC CTG AAG<br>Arg Phe Leu Gln Gly Tyr Phe Gly Gly Asn Leu Lys Arg Tyr Leu Lys<br>         355                360               365 | 1165 |
| TCT GAC CCT ATC CCA GAG AGC AAT GAT GGG CCT GTG AAG GTA GTG GTA<br>Ser Asp Pro Ile Pro Glu Ser Asn Asp Gly Pro Val Lys Val Val Val<br>         370                375               380 | 1213 |

```
GCA GAG AAT TTT GAT GAA ATA GTG AAT AAT GAA AAT AAA GAT GTG CTG        1261
Ala Glu Asn Phe Asp Glu Ile Val Asn Asn Glu Asn Lys Asp Val Leu
            385                 390                 395

ATT GAA TTT TAT GCC CCT TGG TGT GGT CAT TGT AAG AAC CTG GAG CCC        1309
Ile Glu Phe Tyr Ala Pro Trp Cys Gly His Cys Lys Asn Leu Glu Pro
    400                 405                 410

AAG TAT AAA GAA CTT GGC GAG AAG CTC AGC AAA GAC CCA AAT ATC GTC        1357
Lys Tyr Lys Glu Leu Gly Glu Lys Leu Ser Lys Asp Pro Asn Ile Val
415                 420                 425                 430

ATA GCC AAG ATG GAT GCC ACA GCC AAT GAT GTG CCT TCT CCA TAT GAA        1405
Ile Ala Lys Met Asp Ala Thr Ala Asn Asp Val Pro Ser Pro Tyr Glu
                435                 440                 445

GTC AGA GGT TTT CCT ACC ATA TAC TTC TCT CCA GCC AAC AAG AAG CTA        1453
Val Arg Gly Phe Pro Thr Ile Tyr Phe Ser Pro Ala Asn Lys Lys Leu
            450                 455                 460

AAT CCA AAG AAA TAT GAA GGT GGC CGT GAA TTA AGT GAT TTT ATT AGC        1501
Asn Pro Lys Lys Tyr Glu Gly Gly Arg Glu Leu Ser Asp Phe Ile Ser
        465                 470                 475

TAT CTA CAA AGA GAA GCT ACA AAC CCC CCT GTA ATT CAA GAA GAA AAA        1549
Tyr Leu Gln Arg Glu Ala Thr Asn Pro Pro Val Ile Gln Glu Glu Lys
    480                 485                 490

CCC AAG AAG AAG AAG GCA CAG GAG GAT CTC TAA AGCAGTAGCC                 1595
Pro Lys Lys Lys Lys Ala Gln Glu Asp Leu *
495                 500                 505

AAACACCACT TTGTAAAAGG ACTCTTCCAT CAGAGATGGA AAACCATTGG GGAGGGACTA     1655

GGACCCATAT GGGAATTATT ACCTCTCAGG GCCGAGAGGA CAGAATGGAA ATAATCTGAA     1715

TCCTGTTAAA TTTTCTCTAA ACTGTTTCTT AGCTGCACTG TTTATGGAAA TACCAGGAAC     1775

CAGTTTATGT TTGTGGTTTT GGGAAAAATT ATTTGTGTTG GGGGAAATGT TGTGGGGGTG     1835

GGGTTGAGTT GGGGGATATT TTCTAATTTT TTTTGTACAT TTGGAACAGT GACCAATAAA     1895

TGAGACCCCT TTAAACTGTC AAAAAAAAAA AAAAAAA                              1933

(2) INFORMATION FOR SEQ ID NO:2:

(i) SEQUENCE CHARACTERISTICS:
            (A) LENGTH:  506 amino acids
            (B) TYPE: amino acid
            (D) TOPOLOGY: linear (ii) MOLECULE TYPE: protein (xi) SEQUENCE DESCRIPTION: SEQ ID NO:2:

Met Arg Leu Arg Arg Leu Ala Leu Phe Pro Gly Val Ala Leu Leu Leu
 1               5                  10                  15

Ala Ala Ala Arg Leu Ala Ala Ala Ser Asp Val Leu Glu Leu Thr Asp
                20                  25                  30

Asp Asn Phe Glu Ser Arg Ile Ser Asp Thr Gly Ser Ala Gly Leu Met
            35                  40                  45

Leu Val Glu Phe Phe Ala Pro Trp Cys Gly His Cys Lys Arg Leu Ala
        50                  55                  60

Pro Glu Tyr Glu Ala Ala Ala Thr Arg Leu Lys Gly Ile Val Pro Leu
65                  70                  75                  80

Ala Lys Val Asp Cys Thr Ala Asn Thr Asn Thr Cys Asn Lys Tyr Gly
                85                  90                  95

Val Ser Gly Tyr Pro Thr Leu Lys Ile Phe Arg Asp Gly Glu Glu Ala
            100                 105                 110

Gly Ala Tyr Asp Gly Pro Arg Thr Ala Asp Gly Ile Val Ser His Leu
```

-continued

```
            115                 120                 125
Lys Lys Gln Ala Gly Pro Ala Ser Val Pro Leu Arg Thr Glu Glu Glu
        130                 135                 140

Phe Lys Lys Phe Ile Ser Asp Lys Asp Ala Ser Ile Val Gly Phe Phe
145                 150                 155                 160

Asp Asp Ser Phe Ser Glu Ala His Ser Glu Phe Leu Lys Ala Ala Ser
                165                 170                 175

Asn Leu Arg Asp Asn Tyr Arg Phe Ala His Thr Asn Val Glu Ser Leu
            180                 185                 190

Val Asn Glu Tyr Asp Asp Asn Gly Glu Gly Ile Ile Leu Phe Arg Pro
        195                 200                 205

Ser His Leu Thr Asn Lys Phe Glu Tyr Lys Thr Val Ala Tyr Thr Glu
    210                 215                 220

Gln Lys Met Thr Ser Gly Lys Ile Lys Lys Phe Ile Gln Glu Asn Ile
225                 230                 235                 240

Phe Gly Ile Cys Pro His Met Thr Glu Asp Asn Lys Asp Leu Ile Gln
                245                 250                 255

Gly Lys Asp Leu Leu Ile Ala Tyr Tyr Asp Val Asp Tyr Glu Lys Asp
            260                 265                 270

Ala Lys Gly Ser Asn Tyr Trp Arg Asn Arg Val Met Met Val Ala Lys
        275                 280                 285

Lys Phe Leu Asp Ala Gly His Lys Leu Asn Phe Ala Val Ala Ser Arg
290                 295                 300

Lys Thr Phe Ser His Glu Leu Ser Asp Phe Gly Leu Glu Ser Thr Ala
305                 310                 315                 320

Gly Glu Ile Pro Val Val Ala Ile Arg Thr Ala Lys Gly Glu Lys Phe
                325                 330                 335

Val Met Gln Glu Glu Phe Ser Arg Asp Gly Lys Ala Leu Glu Arg Phe
            340                 345                 350

Leu Gln Gly Tyr Phe Gly Gly Asn Leu Lys Arg Tyr Leu Lys Ser Asp
        355                 360                 365

Pro Ile Pro Glu Ser Asn Asp Gly Pro Val Lys Val Val Ala Glu
    370                 375                 380

Asn Phe Asp Glu Ile Val Asn Asn Glu Asn Lys Asp Val Leu Ile Glu
385                 390                 395                 400

Phe Tyr Ala Pro Trp Cys Gly His Cys Lys Asn Leu Glu Pro Lys Tyr
                405                 410                 415

Lys Glu Leu Gly Glu Lys Leu Ser Lys Asp Pro Asn Ile Val Ile Ala
            420                 425                 430

Lys Met Asp Ala Thr Ala Asn Asp Val Pro Ser Pro Tyr Glu Val Arg
        435                 440                 445

Gly Phe Pro Thr Ile Tyr Phe Ser Pro Ala Asn Lys Lys Leu Asn Pro
450                 455                 460

Lys Lys Tyr Glu Gly Gly Arg Glu Leu Ser Asp Phe Ile Ser Tyr Leu
465                 470                 475                 480

Gln Arg Glu Ala Thr Asn Pro Pro Val Ile Gln Glu Glu Lys Pro Lys
                485                 490                 495

Lys Lys Lys Lys Ala Gln Glu Asp Leu *
            500                 505
```

(2) INFORMATION FOR SEQ ID NO:3:

(i) SEQUENCE CHARACTERISTICS:
        (A) LENGTH: 1942 base pairs

-continued

```
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 84..1601

(xi) SEQUENCE DESCRIPTION: SEQ ID NO:3:

GGGTACGTGG TTGCCGGCCC GGTCTCCGCA GTCCCCACCG AGCCCCGACC CTCCTGGCCG           60

CCCCCTCGCC TTACCTCGTC GCC ATG CGC CTC CGC CGC CTA GCG CTG TTC             110
                         Met Arg Leu Arg Arg Leu Ala Leu Phe
                           1               5

CCA GGC CTG GCG CTG CTC CTC GCC GCG GCC CGC CTC GCT GCT GCC TCC           158
Pro Gly Leu Ala Leu Leu Leu Ala Ala Ala Arg Leu Ala Ala Ala Ser
 10              15                  20                  25

GAT GTG CTG GAA CTC ACG GAC GAC AAC TTC GAG AGT CGC ATC ACC GAC           206
Asp Val Leu Glu Leu Thr Asp Asp Asn Phe Glu Ser Arg Ile Thr Asp
                 30                  35                  40

ACG GGC TCT TCT GGC CTC ATG CTC GTC GAG TTC TTC GCC CCC TGG TGT           254
Thr Gly Ser Ser Gly Leu Met Leu Val Glu Phe Phe Ala Pro Trp Cys
                 45                  50                  55

GGA CAC TGC AAA AAG CTT GCC CCA GAG TAT GAA GCT GCA GCT ACC AGA           302
Gly His Cys Lys Lys Leu Ala Pro Glu Tyr Glu Ala Ala Ala Thr Arg
             60                  65                  70

TTA AAA GGA ATA GTC CCG TTA GCA AAG GTG GAT TGT ACT GCC AAC ACG           350
Leu Lys Gly Ile Val Pro Leu Ala Lys Val Asp Cys Thr Ala Asn Thr
 75                  80                  85

AAC ACC TGT AAT AAG TAT GGA GTG AGT GGA TAT CCA ACC CTG AAG ATA           398
Asn Thr Cys Asn Lys Tyr Gly Val Ser Gly Tyr Pro Thr Leu Lys Ile
 90                  95                 100                 105

TTT AGA GAT GGT GAA GAA TCA GGT GCC TAT GAT GGG CCT AGG ACT GCC           446
Phe Arg Asp Gly Glu Glu Ser Gly Ala Tyr Asp Gly Pro Arg Thr Ala
                 110                 115                 120

GAT GGA ATT GTC AGC CAC CTG AAG AAA CAG GCT GGA CCA GCT TCA GTT           494
Asp Gly Ile Val Ser His Leu Lys Lys Gln Ala Gly Pro Ala Ser Val
                 125                 130                 135

CCT CTC AAG TCT GAG GAA GAA TTT GAA AAG TTC ATT AGC GAT AAA GAT           542
Pro Leu Lys Ser Glu Glu Glu Phe Glu Lys Phe Ile Ser Asp Lys Asp
                 140                 145                 150

GCT TCT GTG GTG GGT TTT TTC AAG GAT TTA TTC AGT GAA GCT CAC TCT           590
Ala Ser Val Val Gly Phe Phe Lys Asp Leu Phe Ser Glu Ala His Ser
 155                 160                 165

GAG TTT CTA AAA GCA GCC AGC AAC TTG AGG GAT AAC TAC CGG TTT GCA           638
Glu Phe Leu Lys Ala Ala Ser Asn Leu Arg Asp Asn Tyr Arg Phe Ala
 170                 175                 180                 185

CAC ACC AAT GTT GAA TCT CTG GTG AAC AAA TAC GAT GAC GAT GGA GAG           686
His Thr Asn Val Glu Ser Leu Val Asn Lys Tyr Asp Asp Asp Gly Glu
                 190                 195                 200

GGT ATC ACC TTG TTT CGT CCT TCC CAT CTG ACG AAC AAG TTT GAA GAC           734
Gly Ile Thr Leu Phe Arg Pro Ser His Leu Thr Asn Lys Phe Glu Asp
                 205                 210                 215

AAG ACT GTG GCA TAT ACA GAA CAG AAA ATG ACC AGT GGG AAG ATT AAA           782
Lys Thr Val Ala Tyr Thr Glu Gln Lys Met Thr Ser Gly Lys Ile Lys
                 220                 225                 230

AGA TTT ATT CAG GAA AAC ATT TTT GGT ATC TGC CCT CAC ATG ACA GAA           830
Arg Phe Ile Gln Glu Asn Ile Phe Gly Ile Cys Pro His Met Thr Glu
 235                 240                 245

GAC AAT AAA GAT TTA CTA CAG GGC AAG GAT TTA CTC ATC GCT TAC TAT           878
```

```
Asp Asn Lys Asp Leu Leu Gln Gly Lys Asp Leu Leu Ile Ala Tyr Tyr
250                 255                 260                 265

GAT GTG GAC TAT GAA AAG AAT GCT AAA GGT TCC AAC TAC TGG AGA AAC          926
Asp Val Asp Tyr Glu Lys Asn Ala Lys Gly Ser Asn Tyr Trp Arg Asn
                        270                 275                 280

AGA GTA ATG ATG GTG GCA AAG AAA TTC CTG GAT GCT GGG CAG AAA CTC          974
Arg Val Met Met Val Ala Lys Lys Phe Leu Asp Ala Gly Gln Lys Leu
                285                 290                 295

CAT TTT GCT GTA GCT AGC CGT AAA ACC TTT AGC CAT GAA CTT TCA GAT         1022
His Phe Ala Val Ala Ser Arg Lys Thr Phe Ser His Glu Leu Ser Asp
        300                 305                 310

TTT GGC TTG GAA AGC ACT ACT GGA GAG ATT CCT GTT GTT GCT GTC AGA         1070
Phe Gly Leu Glu Ser Thr Thr Gly Glu Ile Pro Val Val Ala Val Arg
315                 320                 325

ACC GCA AAA GGA GAG AAG TTT GTC ATG CAG GAG GAG TTC TCG CGT GAT         1118
Thr Ala Lys Gly Glu Lys Phe Val Met Gln Glu Glu Phe Ser Arg Asp
330                 335                 340                 345

GGC AAG GCT CTT GAG AGA TTC CTG GAG GAT TAC TTT GAC GGC AAC CTG         1166
Gly Lys Ala Leu Glu Arg Phe Leu Glu Asp Tyr Phe Asp Gly Asn Leu
                350                 355                 360

AAG AGA TAC CTG AAG TCT GAG CCT ATC CCT GAG AGC AAT GAT GGG CCT         1214
Lys Arg Tyr Leu Lys Ser Glu Pro Ile Pro Glu Ser Asn Asp Gly Pro
        365                 370                 375

GTA AAG GTA GTG GTA GCA GAG AAT TTT GAT GAA ATA GTG AAT AAT GAA         1262
Val Lys Val Val Val Ala Glu Asn Phe Asp Glu Ile Val Asn Asn Glu
380                 385                 390

AAT AAA GAT GTG CTG ATT GAG TTT TAT GCT CCT TGG TGT GGT CAC TGT         1310
Asn Lys Asp Val Leu Ile Glu Phe Tyr Ala Pro Trp Cys Gly His Cys
            395                 400                 405

AAG AAT CTG GAG CCT AAG TAT AAA GAA CTG GGA GAG AAG CTC AGA AAA         1358
Lys Asn Leu Glu Pro Lys Tyr Lys Glu Leu Gly Glu Lys Leu Arg Lys
410                 415                 420                 425

GAT CCA AAT ATT GTC ATA GCC AAG ATG GAT GCT ACA GCC AAC GAT GTG         1406
Asp Pro Asn Ile Val Ile Ala Lys Met Asp Ala Thr Ala Asn Asp Val
                430                 435                 440

CCT TCT CCA TAT GAA GTC AGA GGT TTT CCT ACC ATC TAC TTC TCT CCA         1454
Pro Ser Pro Tyr Glu Val Arg Gly Phe Pro Thr Ile Tyr Phe Ser Pro
        445                 450                 455

GCC AAC AAG AAG CAA AAT CCA AAG AAA TAT GAA GGT GGC CGT GAA TTA         1502
Ala Asn Lys Lys Gln Asn Pro Lys Lys Tyr Glu Gly Gly Arg Glu Leu
460                 465                 470

AGT GAT TTT ATT AGC TAT CTA AAG CGA GAG GCT ACA AAC CCC CCT GTA         1550
Ser Asp Phe Ile Ser Tyr Leu Lys Arg Glu Ala Thr Asn Pro Pro Val
            475                 480                 485

ATT CAA GAA GAA AAA CCC AAG AAG AAG AAG GCA CAG GAG GAT CTC             1598
Ile Gln Glu Glu Lys Pro Lys Lys Lys Lys Ala Gln Glu Asp Leu
490                 495                 500                 505

TAA AGCAGCAGCC AAACATCATA TACTTTGTCA AAGGACTTTT CCACCAGAGA              1651
*

TGGGAAAACC AATGGGGAGG ACTGGGACCC GTATGGGAAT TACTGCCTCT CAGGGCTGAG       1711

AGGGCAGAAT GGTTATAATC TGAGTCCTGT TAAATTTTCT CTAAACTGTT TCTTAGCTGC       1771

ACTGTTTATG AAAATACCAG AACCAGTTTA TGTTTGTGGT TTTGGGAAAA TTATTTGTGT       1831

TGAGGGGAAT GTTGTGGGGG TGGGGGGAAT TGAGTTGGGG GGTTATTTTC TAATTTTTTT       1891

TGTACATTTG GAACAGTGAC AATAAATGCG CCCCCTTTAA AAAAAAAAA A                 1942

(2) INFORMATION FOR SEQ ID NO:4:
```

(i) SEQUENCE CHARACTERISTICS:
    (A) LENGTH: 506 amino acids
    (B) TYPE: amino acid
    (D) TOPOLOGY: linear (ii) MOLECULE TYPE: protein (xi) SEQUENCE DESCRIPTION: SEQ ID NO:4:

```
Met Arg Leu Arg Arg Leu Ala Leu Phe Pro Gly Leu Ala Leu Leu Leu
 1               5                  10                  15

Ala Ala Ala Arg Leu Ala Ala Ala Ser Asp Val Leu Glu Leu Thr Asp
            20                  25                  30

Asp Asn Phe Glu Ser Arg Ile Thr Asp Thr Gly Ser Ser Gly Leu Met
        35                  40                  45

Leu Val Glu Phe Phe Ala Pro Trp Cys Gly His Cys Lys Lys Leu Ala
 50                  55                  60

Pro Glu Tyr Glu Ala Ala Ala Thr Arg Leu Lys Gly Ile Val Pro Leu
 65                  70                  75                  80

Ala Lys Val Asp Cys Thr Ala Asn Thr Asn Thr Cys Asn Lys Tyr Gly
                85                  90                  95

Val Ser Gly Tyr Pro Thr Leu Lys Ile Phe Arg Asp Gly Glu Glu Ser
            100                 105                 110

Gly Ala Tyr Asp Gly Pro Arg Thr Ala Asp Gly Ile Val Ser His Leu
        115                 120                 125

Lys Lys Gln Ala Gly Pro Ala Ser Val Pro Leu Lys Ser Glu Glu Glu
130                 135                 140

Phe Glu Lys Phe Ile Ser Asp Lys Asp Ala Ser Val Val Gly Phe Phe
145                 150                 155                 160

Lys Asp Leu Phe Ser Glu Ala His Ser Glu Phe Leu Lys Ala Ala Ser
                165                 170                 175

Asn Leu Arg Asp Asn Tyr Arg Phe Ala His Thr Asn Val Glu Ser Leu
            180                 185                 190

Val Asn Lys Tyr Asp Asp Gly Glu Gly Ile Thr Leu Phe Arg Pro
            195                 200                 205

Ser His Leu Thr Asn Lys Phe Glu Asp Lys Thr Val Ala Tyr Thr Glu
210                 215                 220

Gln Lys Met Thr Ser Gly Lys Ile Lys Arg Phe Ile Gln Glu Asn Ile
225                 230                 235                 240

Phe Gly Ile Cys Pro His Met Thr Glu Asp Asn Lys Asp Leu Leu Gln
                245                 250                 255

Gly Lys Asp Leu Leu Ile Ala Tyr Tyr Asp Val Asp Tyr Glu Lys Asn
            260                 265                 270

Ala Lys Gly Ser Asn Tyr Trp Arg Asn Arg Val Met Met Val Ala Lys
        275                 280                 285

Lys Phe Leu Asp Ala Gly Gln Lys Leu His Phe Ala Val Ala Ser Arg
290                 295                 300

Lys Thr Phe Ser His Glu Leu Ser Asp Phe Gly Leu Glu Ser Thr Thr
305                 310                 315                 320

Gly Glu Ile Pro Val Val Ala Val Arg Thr Ala Lys Gly Glu Lys Phe
                325                 330                 335

Val Met Gln Glu Glu Phe Ser Arg Asp Gly Lys Ala Leu Glu Arg Phe
            340                 345                 350

Leu Glu Asp Tyr Phe Asp Gly Asn Leu Lys Arg Tyr Leu Lys Ser Glu
        355                 360                 365

Pro Ile Pro Glu Ser Asn Asp Gly Pro Val Lys Val Val Val Ala Glu
```

```
        370             375             380
Asn Phe Asp Glu Ile Val Asn Asn Glu Asn Lys Asp Val Leu Ile Glu
385                 390                 395                 400

Phe Tyr Ala Pro Trp Cys Gly His Cys Lys Asn Leu Glu Pro Lys Tyr
                405                 410                 415

Lys Glu Leu Gly Glu Lys Leu Arg Lys Asp Pro Asn Ile Val Ile Ala
                420                 425                 430

Lys Met Asp Ala Thr Ala Asn Asp Val Pro Ser Pro Tyr Glu Val Arg
                435                 440                 445

Gly Phe Pro Thr Ile Tyr Phe Ser Pro Ala Asn Lys Lys Gln Asn Pro
                450                 455                 460

Lys Lys Tyr Glu Gly Gly Arg Glu Leu Ser Asp Phe Ile Ser Tyr Leu
465                 470                 475                 480

Lys Arg Glu Ala Thr Asn Pro Pro Val Ile Gln Glu Glu Lys Pro Lys
                    485                 490                 495

Lys Lys Lys Lys Ala Gln Glu Asp Leu  *
                500                 505
```

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS:
        (D) TOPOLOGY: Not Relevant (ii) MOLECULE TYPE: peptide (xi) SEQUENCE DESCRIPTION: SEQ ID NO:5:

```
Trp Cys Gly His Cys Lys
1               5
```

(2) INFORMATION FOR SEQ ID NO:6:

(i) SEQUENCE CHARACTERISTICS:
        (A) LENGTH: 6 amino acids
        (B) TYPE: amino acid
        (C) STRANDEDNESS:
        (D) TOPOLOGY: Not Relevant (ii) MOLECULE TYPE: peptide (xi) SEQUENCE DESCRIPTION: SEQ ID NO:6:

```
Trp Cys Gly Pro Cys Lys
1               5
```

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "mutagenic primer"

(xi) SEQUENCE DESCRIPTION: SEQ ID NO:7:

```
GCCCCCTGGT CTCCACACAG CAAAAAGCTT                              30
```

(2) INFORMATION FOR SEQ ID NO:8:

(i) SEQUENCE CHARACTERISTICS:
        (A) LENGTH: 30 base pairs

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "mutagenic primer"

(xi) SEQUENCE DESCRIPTION: SEQ ID NO:8:

GCTCCTTGGT CTGGTCACTC TAAGAATCTG                                         30
```